(12) United States Patent
Bowe

(10) Patent No.: US 8,118,854 B2
(45) Date of Patent: Feb. 21, 2012

(54) ENDOVASCULAR DELIVERY DEVICE

(75) Inventor: Jason S. Bowe, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 697 days.

(21) Appl. No.: 11/904,834

(22) Filed: Sep. 28, 2007

(65) Prior Publication Data

US 2008/0109065 A1 May 8, 2008

Related U.S. Application Data

(60) Provisional application No. 60/847,708, filed on Sep. 28, 2006.

(51) Int. Cl.
*A61F 2/06* (2006.01)

(52) U.S. Cl. ...................... 623/1.11; 623/1.23

(58) Field of Classification Search ................. 623/1.11, 623/1.12, 1.23
See application file for complete search history.

(56) References Cited

U.S. PATENT DOCUMENTS

| 5,782,909 | A * | 7/1998 | Quiachon et al. ............. 606/194 |
| 6,346,118 | B1 * | 2/2002 | Baker et al. .................. 623/1.12 |
| 6,379,365 | B1 * | 4/2002 | Diaz .............................. 606/108 |
| 6,641,606 | B2 * | 11/2003 | Ouriel et al. .................. 623/1.12 |
| 2003/0144670 | A1 * | 7/2003 | Pavcnik et al. ............... 606/108 |
| 2004/0097965 | A1 | 5/2004 | Gardeski et al. |
| 2004/0098084 | A1 * | 5/2004 | Hartley et al. ............... 623/1.11 |
| 2004/0230287 | A1 * | 11/2004 | Hartley et al. ............... 623/1.12 |
| 2006/0004433 | A1 * | 1/2006 | Greenberg et al. .......... 623/1.11 |
| 2006/0155358 | A1 * | 7/2006 | LaDuca et al. ............... 623/1.11 |
| 2006/0178726 | A1 | 8/2006 | Douglas |
| 2007/0043425 | A1 | 2/2007 | Hartley et al. |
| 2007/0299499 | A1 * | 12/2007 | Hartley et al. ............... 623/1.11 |

FOREIGN PATENT DOCUMENTS

| WO | WO 03/002033 A1 | 1/2003 |
| WO | WO 2004/071352 A1 | 8/2004 |
| WO | WO 2004/089249 A1 | 10/2004 |
| WO | WO 2005/068007 A2 | 7/2005 |

* cited by examiner

*Primary Examiner* — Gary Jackson
*Assistant Examiner* — Jonathan Hollm
(74) *Attorney, Agent, or Firm* — Richard J. Godlewski

(57) ABSTRACT

An endovascular delivery device (2) for a stent graft which has a pusher catheter (4), a flexible sheath (10) over the pusher catheter and at least one auxiliary catheter (32) extending between the pusher catheter and the flexible sheath. The pusher catheter has one or more longitudinal grooves (30) on its outside surface and the auxiliary catheter or catheters extend along the longitudinal grooves. A guide wire in the auxiliary catheter can be used to pre-catheterize a fenestration in the stent graft and a branch stent or stent graft delivered through the auxiliary catheter.

7 Claims, 6 Drawing Sheets

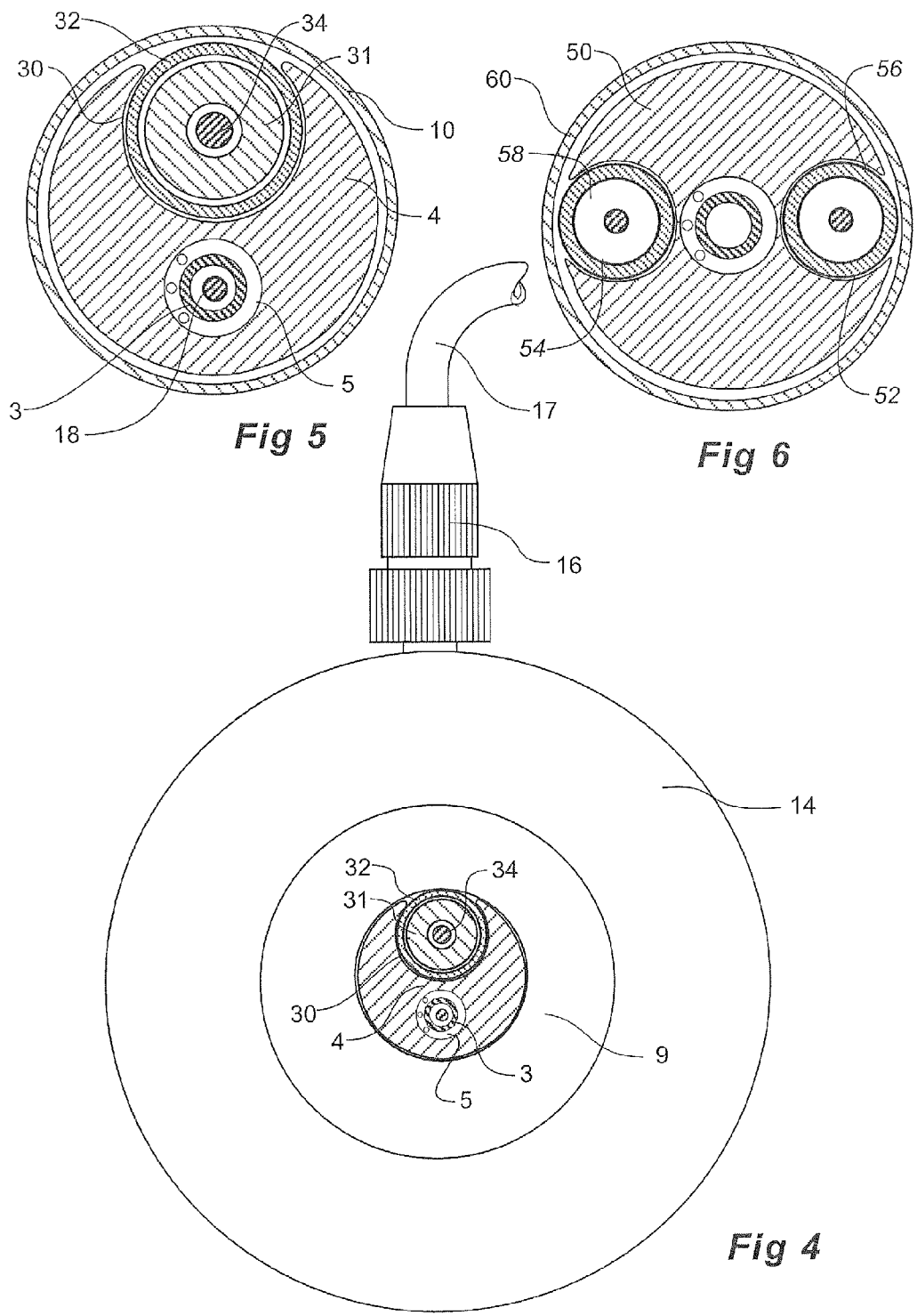

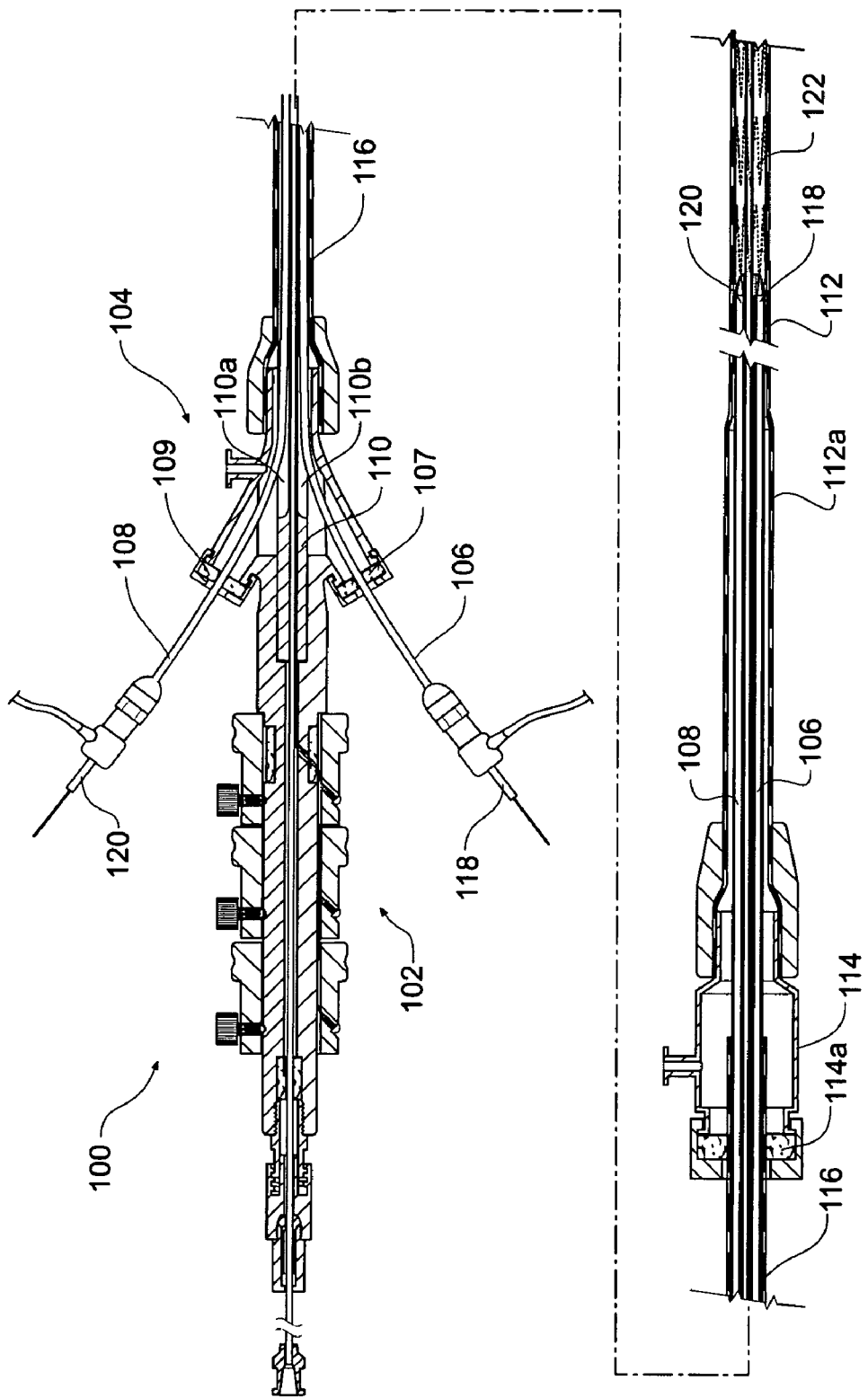

ENDOVASCULAR DELIVERY DEVICE

CROSS-REFERENCE TO RELATED APPLICATIONS

This application claims priority of provisional application Ser. No. 60/847,708, filed Sep. 28, 2006.

TECHNICAL FIELD

This invention relates to a stent graft delivery device and more particularly to a delivery device including an indwelling catheter.

BACKGROUND OF THE INVENTION

This invention will be particularly discussed in relation to deployment devices for placement of stent grafts into the thoracoabdominal aorta for the treatment of aneurysms and more specifically in relation to juxtarenal placement. The invention, however, is not so restricted and may be applied to stent grafts for placement in any lumen of the human or animal body.

Surgical repair of the thoracoabdominal aorta often involves wide exposure through long, multi-cavity incisions, followed by periods of visceral ischemia. Despite advances in surgical technique and perioperative care, the mortality and morbidity rates remain high, especially in patients who are old, sick, or have already undergone open surgical repair of an adjacent segment of the aorta. In such cases, an endovascular alternative would be welcome, yet endovascular methods of thoracoabdominal and pararenal aortic repair have been slow to develop. The challenge has been to exclude the aortic aneurysm while maintaining flow to its visceral branches.

Two distinctly different approaches to this problem have been reported. The two devices were: a bifurcated abdominal aortic stent-graft with fenestrations for the renal and superior mesenteric arteries, and a thoracoabdominal stent-graft with branches for the celiac, superior mesenteric and renal arteries. In recent years, the distinctions between fenestrated and multi-branched stent-grafts have been bluffed by the emergence of many hybrid devices with features such as Nitinol ringed fenestrations, externally cuffed fenestrations, internally cuffed fenestrations, external spiral cuffs and axially-oriented cuffs or branches, both external and internal. Each element has advantages and disadvantages, and each combination has a different role, as described below.

There now exists a family of devices for treatment of abdominal aortic aneurysms (AAA), which share several key features. In each of them, a barbed uncovered Z-stent anchors the proximal end, and a single proximal orifice attaches to a non-dilated segment of aorta (or previously inserted prosthesis). They all distribute blood through multiple branches, cuffs or holes (fenestrations), and they have series of Z-stents and Nitinol rings, providing support from one end of the stent-graft to the other.

In cases of juxtarenal AAA, the rim of non-dilated infra-renal aorta is too short for secure hemostatic implantation of an unfenestrated stent-graft. There is only enough room in the neck for the proximal end of the proximal stent; the rest of this covered stent expands into the aneurysm, assuming a conical shape. Under these circumstances, there is insufficient apposition between the stent-graft and the aorta to achieve a reliable seal. Properly positioned fenestrations (holes) provide a route for flow through the stent-graft into the renal arteries, thereby allowing the proximal end of the stent-graft to be placed higher in the non-dilated pararenal aorta where it assumes a cylindrical shape. The dual goals of renal perfusion and aneurysm exclusion are achieved only when the fenestration is positioned precisely over the renal orifices, and the outer surface of the stent-graft around the fenestration is brought into close apposition with the inner surface of the aorta around the renal orifice. Typical fenestrated technique uses a bridging catheter, sheath or balloon to guide each fenestration to the corresponding renal orifice, and a bridging stent to hold it there. Stent-graft deployment has five main stages: extrusion of the half-open stent-graft, trans-graft renal artery catheterization, complete stent-graft expansion, renal stenting, and completion of the aortic exclusion with bifurcated extension into the iliac arteries.

The three forms of fenestration in common use are the large fenestration, the scallop and the small fenestration. A large fenestration is used only when the target artery is well away from the aneurysm. No bridging stent is required, or even feasible, since one or more stent struts cross the orifice of a large fenestration. A scallop is essentially a large open-topped fenestration. In many cases, the presence of a scallop for the superior mesenteric artery allows sufficient separation (>15 mm) between proximal margin of the stent-graft and the middle of the renal orifices. Small fenestrations are commonly placed over both renal arteries, and held there by bridging stents. Stent struts cannot cross the orifice of a small fenestration. Small fenestrations are therefore confined to the lower halves of the triangular spaces between adjacent stent-struts.

Localized juxtarenal aneurysms or pseudoaneurysms require no more than a single cylindrical fenestrated stent-graft, but most cases of infrarenal aneurysm extend to the aortic bifurcation and require bilateral iliac outflow through a bifurcated stent-graft. The combination of a fenestrated proximal component with a bifurcated distal component is called a composite stent graft. Dividing the stent-graft into two components separates the two halves of the procedure. The operator need not be concerned about the position or orientation of the bifurcation while inserting the fenestrated proximal component, or about the position and location of the fenestrations while inserting the bifurcated distal component. The composite arrangement also separates the fenestrated proximal component from the large caudally directed haemo-dynamic forces that act mainly upon the bifurcation of the distal component. A small amount of slippage between the two is preferable to any proximal component migration, where even a few millimetres of movement would occlude both renal arteries. Indeed, the low rate of renal artery loss is testimony to the accuracy of stent-graft deployment and the stability of stent-graft attachment.

It is to the problem of trans-graft renal artery catheterization for subsequent renal stenting that the present invention is directed. The invention will be discussed in relation to renal catheterisation but is not so limited.

There can be a problem with placement of a guide wire or catheter through a fenestration and into a renal artery. It can be assisted by pre-catheterisation of the fenestration or fenestrations but the presence of an auxiliary catheter can be a problem. The final stage of stenting a renal artery cannot be achieved until the main body of a deployment device has been removed but the presence of an auxiliary catheter can make this difficult.

It is to this problem that the present invention is directed.

Throughout this specification the term distal with respect to a portion of the aorta, a deployment device or a prosthesis means the end of the aorta, deployment device or prosthesis further away in the direction of blood flow away from the heart and the term proximal means the portion of the aorta, deployment device or end of the prosthesis nearer to the heart. When applied to other vessels similar terms such as caudal and cranial should be understood.

SUMMARY OF THE INVENTION

In one form the invention is said to reside in an endovascular delivery device comprising a pusher catheter, a handle at the distal end of the pusher catheter and a proximal nose cone dilator at the proximal end of the pusher catheter, a flexible sheath over the pusher catheter and extending to the nose cone dilator and thereby retaining a stent graft in a contracted conformation distally of the nose cone dilator, the pusher catheter comprising at least one longitudinal groove on an outside surface thereof and an auxiliary catheter extending between the pusher catheter and the flexible sheath from the handle to the nose cone dilator along the longitudinal groove. The auxiliary catheter can be for catheterising a renal artery for instance.

Preferably the flexible sheath comprises a manipulator and haemostatic seal at the distal end thereof, the haemostatic seal sealing against the pusher catheter and the auxiliary catheter.

The manipulator for the sheath may include auxiliary access ports, each with a hemostatic seal to allow the auxiliary catheters to pass therethrough and be received in the longitudinal groove or grooves in the pusher.

There may be further a guide wire catheter extending from the pusher catheter to and through the nose cone dilator. Preferably the pusher catheter comprises a longitudinal lumen therethrough and the guide wire catheter extends through the longitudinal lumen so that the guide wire catheter is movable longitudinally and rotationally with respect to the pusher catheter and fixed thereto by the use of a pin vice. Preferably the guide wire catheter is offset from the center of the pusher catheter.

There may be further included at least one of a dilator or an auxiliary guide wire extending through the auxiliary catheter. The dilator or auxiliary guide wire is preferably movable with respect to the auxiliary catheter.

Preferably the stent graft comprises a tubular body of a biocompatible material with a lumen therethrough and a plurality of stents, the stent graft being mounted onto the delivery device for deployment therefrom and being positioned on the guide wire catheter distally of the nose cone dilator and proximally of the pusher catheter and the guide wire catheter and auxiliary catheter passing through the lumen of the stent graft. Preferably the stent graft comprises a fenestration and the auxiliary guide wire extends into and through the fenestration to be an indwelling guide wire therein during deployment.

Preferably the auxiliary catheter comprises a dilator extending therein to terminate distal of the stent graft before and during initial deployment and to be advanced through the auxiliary catheter over the auxiliary guide wire during deployment to extend through the fenestration in the stent graft such that the auxiliary catheter can be advanced to extend through the fenestration.

There may be a releasable retention system for a proximal end of the stent graft. The releasable retention system can include a distally opening capsule at the distal end of the nose cone dilator and an exposed proximally extending stent on the stent graft being received in the capsule. There may also be a releasable retention system for a distal end of the stent graft. There may also be a diameter reducing system for the stent graft retained onto the delivery device. The diameter reducing system can include a comprising at least one release wire extending longitudinally along the graft material tube and at least one circumferential thread engaged around the release wire and a portion of the stent graft circumferentially spaced a selected distance away from the release wire and drawn tight and tied to reduce the circumference and hence the overall diameter of the stent graft. The release wire can be retracted to release the circumferential thread or threads.

Suitable diameter reducing systems are taught in co-pending patent application Ser. No. 11/507,115 entitled "Assembly of Stent Grafts" and the teaching therein is incorporated herein it its entirety.

There may be a plurality of longitudinal grooves in the pusher catheter and a plurality of auxiliary catheters therein.

In an alternative form the invention comprises an endovascular delivery device comprising a pusher catheter, a handle at the distal end of the pusher catheter, a proximal nose cone dilator, a guide wire catheter extending from the pusher catheter to and through the nose cone dilator, the pusher catheter comprising a longitudinal lumen therethrough and the guide wire catheter extends through the longitudinal lumen so that the guide wire catheter is movable longitudinally and rotationally with respect to the pusher catheter and fixed thereto by the use of a pin vice, a stent graft on the delivery device proximal of the pusher catheter and distal of the nose cone dilator, a flexible sheath over the pusher catheter and extending to the nose cone dilator and thereby retaining the stent graft in a contracted conformation between the pusher catheter and the nose cone dilator, the pusher catheter comprising at least one longitudinal groove on an outside surface thereof and an auxiliary catheter extending between the pusher catheter and the flexible sheath from the handle to the nose cone dilator along the longitudinal groove.

BRIEF DESCRIPTION OF THE DRAWING

This then generally describes the invention but to assist with understanding reference will now be made to the accompanying drawings which show preferred embodiments of the invention.

In the drawings:

FIG. 4 shows a transverse cross sectional view along the line 4-4' in FIG. 1;

FIG. 5 shows a transverse cross sectional view along the line 5-5' in FIG. 1;

FIG. 6 shows a cross section of a pusher catheter and introducer sheath of an alternative embodiment of the invention;

FIG. 9 shows a cross section of a handle, pusher catheter, hemostatic seal and introducer sheath of an alternative embodiment of the invention.

DETAILED DESCRIPTION

FIGS. 1, 2, 3, 4 and 5 depict a delivery device 2 according to one embodiment of the invention.

Figure 1:
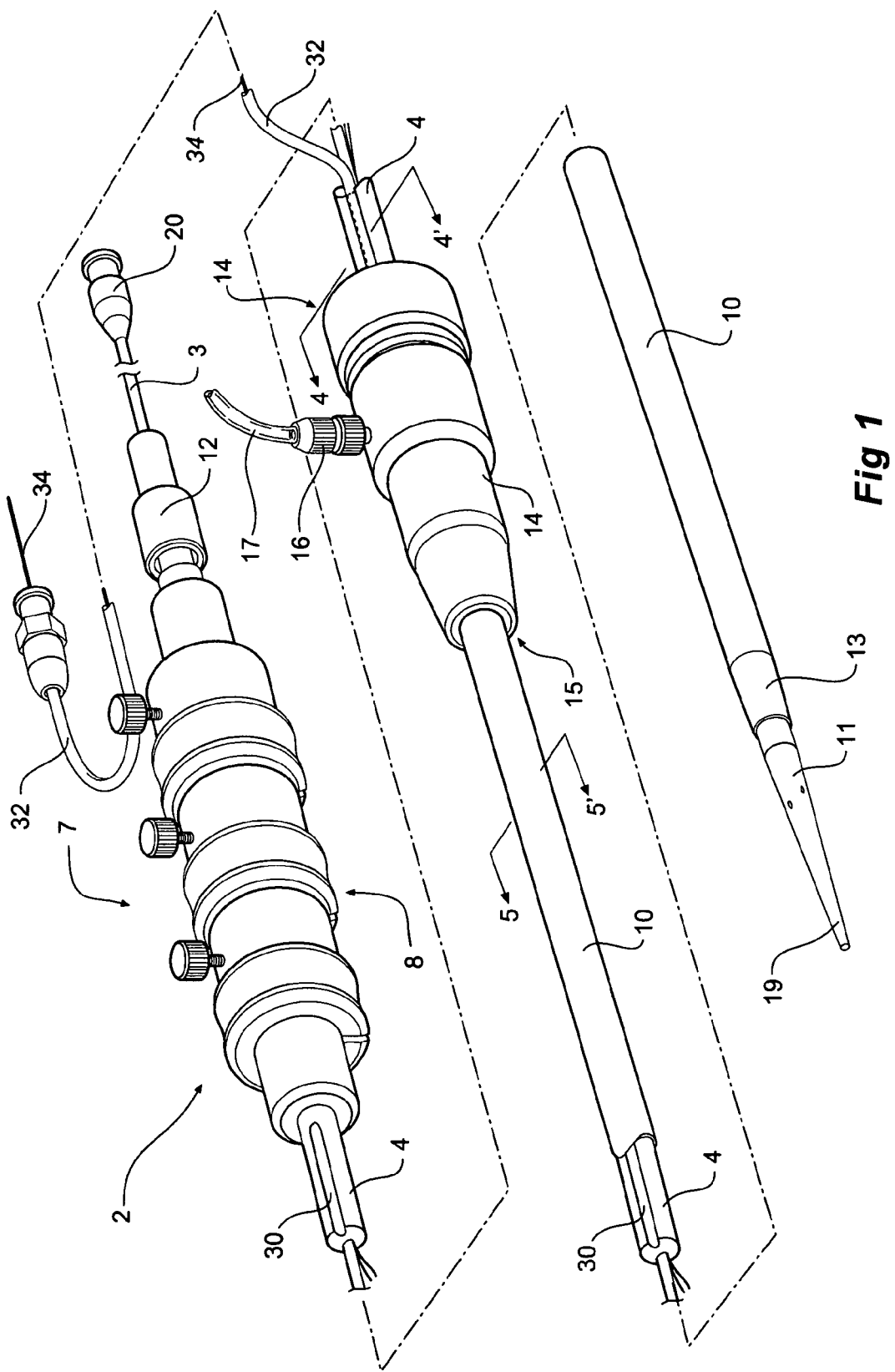
FIG. 1 shows a perspective view of a delivery device according to one embodiment of the invention.
Figure 2:
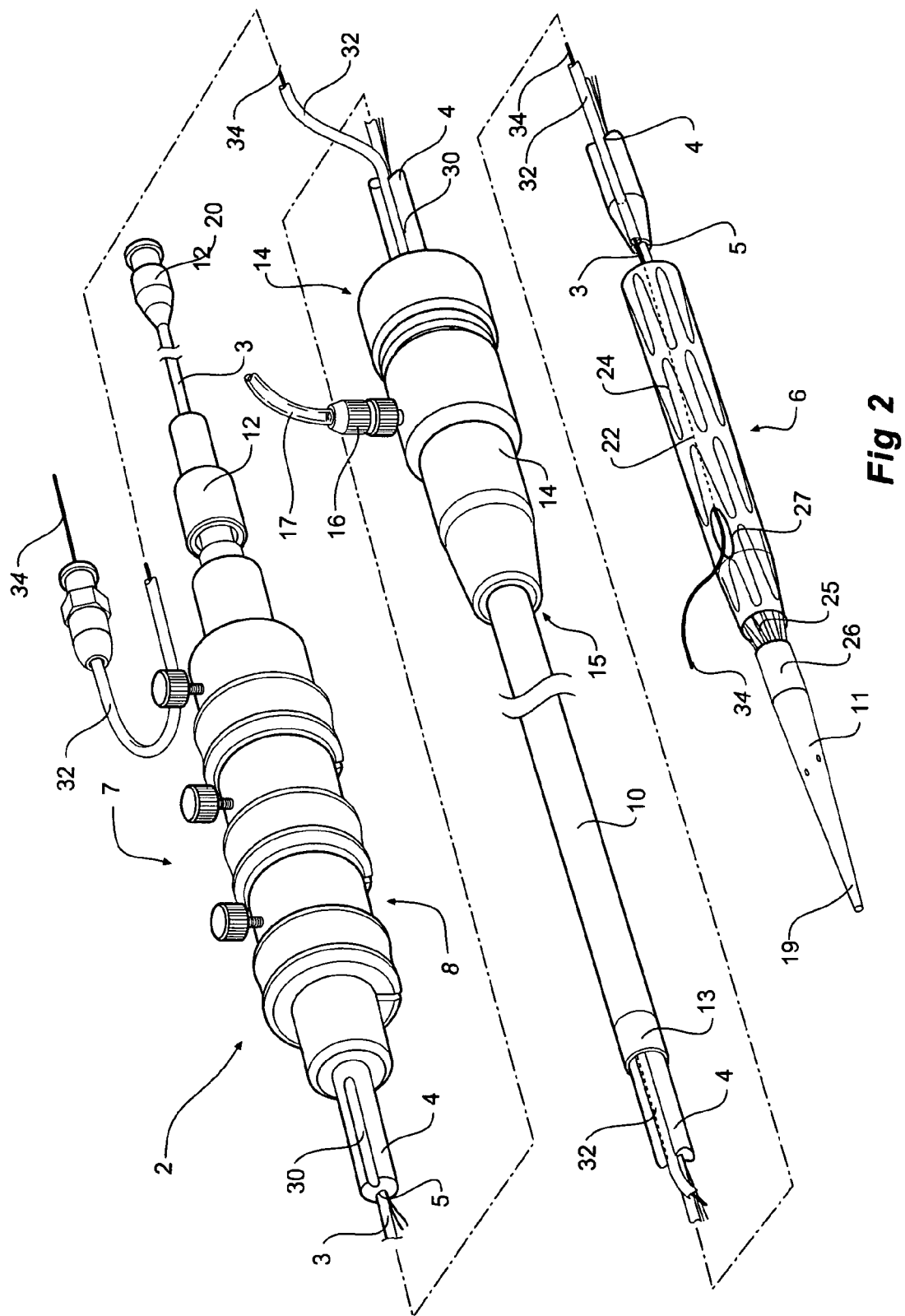
FIG. 2 shows the embodiment of FIG. 1 but with the sheath withdrawn to show the stent graft and pusher catheter.
Figure 3:
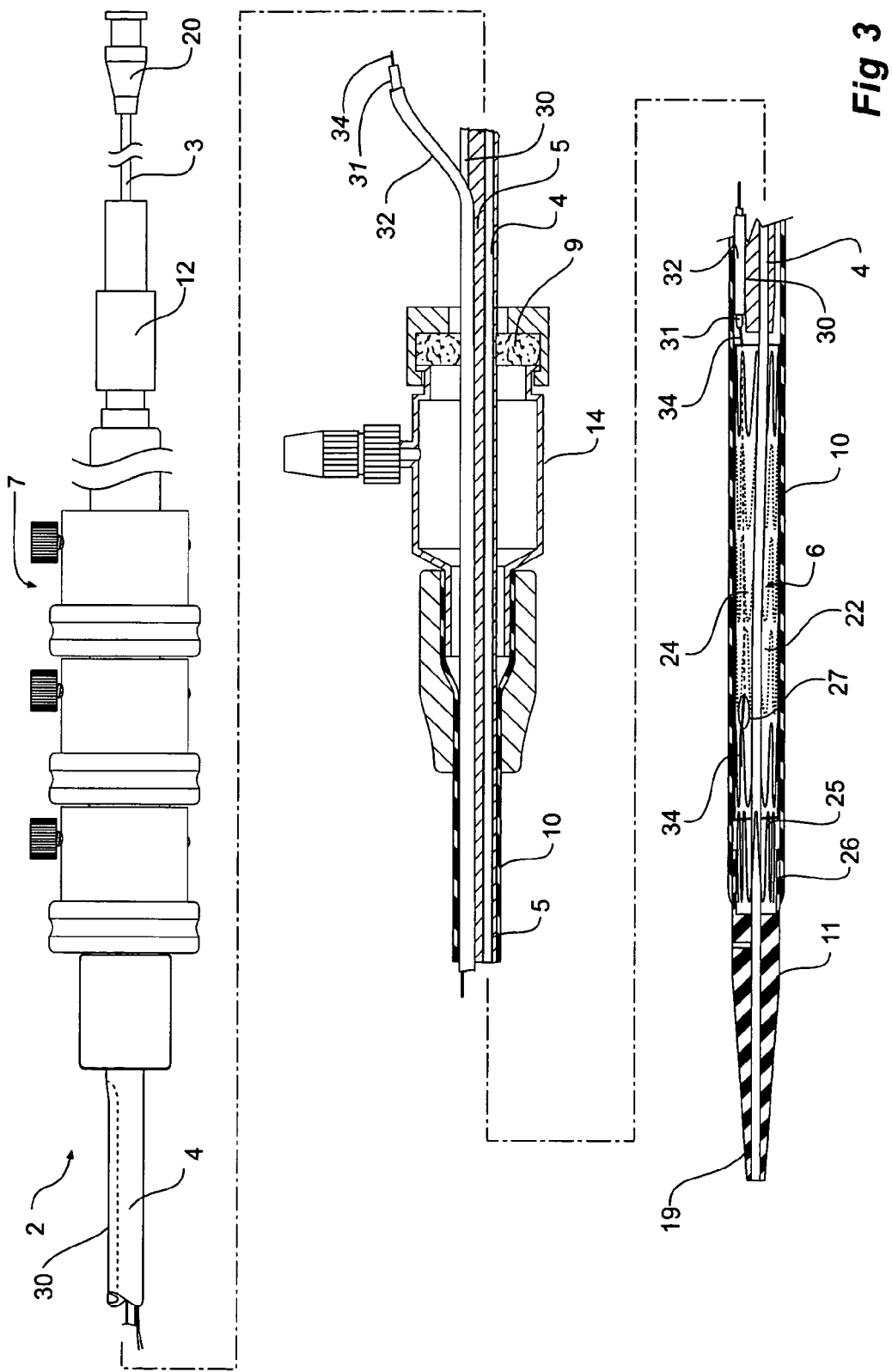
FIG. 3 shows a side view of the device of FIG. 1 with part shown in longitudinal cross section.

FIG. 1 shows a perspective view of a delivery device. FIG. 2 shows the same view as FIG. 1 but with the sheath withdrawn to show the stent graft and pusher catheter. FIG. 3 shows a side view of the device of FIG. 1 with part shown in longitudinal cross section. FIG. 4 shows a transverse cross sectional view along the line 4-4' in FIG. 1. FIG. 5 shows a transverse cross sectional view along the line 5-5' in FIG. 1.

The delivery device 2 has a guide wire catheter 3 which extends from distal of a handle 7 to and through a proximal tapered nose cone dilator 11. The guide wire catheter 3 extends longitudinally through a passageway or lumen 5 of a pusher or delivery catheter 4 which is connected to the handle 7 at its distal end. It will be particularly noted in FIGS. 3 and 4 that the lumen 5 in the pusher catheter for the guide wire catheter is offset from the center of the pusher catheter 4. The guide wire catheter 3 can move longitudinally and rotationally with respect to the pusher catheter 4 and can be fixed with respect to the pusher catheter 4 by a pin vice 12 at the distal end of the handle 7. An introducer sheath 10 fits coaxially around the delivery catheter 4 and extends from a tapered proximal end 13 which optionally includes a radiopaque marker (not shown) to a connector valve and manipulator 14 attached about distal end 15 of the sheath.

The connector valve and manipulator 14 may be an automatically sealing valve comprising a haemostatic seal assembly including a silicone disc assembly and the pusher catheter and the auxiliary catheter extending through the silicone disc assembly. Alternatively the valve assembly can include a manually operable valve such as the Captor Valve (Cook Inc, Bloomington, Ind.)

The introducer sheath 10 extends proximally to the nose cone dilator 11 and covers the stent graft 6 as is shown in FIG. 1 during introduction of the deployment device into a patient. The introducer sheath 10 is withdrawn distally to expose the stent graft 6 as is shown in FIG. 2 during deployment when the deployment device is in a selected position within the vasculature of a patient. A well-known male Luer lock connector hub 20 is attached at the distal end of the guide wire catheter 10 for connection to syringes and other medical apparatus.

The stent graft or implantable device 6 is carried on the guide wire catheter 3 proximally of the delivery catheter 4 and distally of the nose cone dilator 11. Connector valve and manipulator 14 includes a silicone disk 9 which seals against the pusher catheter 4 for preventing the backflow of fluids therethrough. The disk 9 includes a slit for the insertion of the nose cone dilator 11 and pusher catheter 4. Connector valve and manipulator 14 also includes side arm 16 to which tube 17 is connected for introducing and aspirating fluids therethrough. Nose cone dilator 11 includes a tapered proximal end 19 for accessing and dilating a vascular access site over a well-known and commercially available wire guide 9 (see FIG. 5) extending through the guide wire catheter.

Along the length of the pusher catheter 4 from just proximal of the handle 7 to the proximal end of the pusher catheter 4 is a longitudinal groove 30. Into the groove 30 is received an auxiliary catheter 32. Through a lumen of the auxiliary catheter 32 extends a dilator 31 and an auxiliary guide wire 34 through a lumen of the dilator. In effect as can be particularly seen in FIG. 5 the auxiliary catheter 32 is retained between the pusher catheter 4 and the sheath 10.

The auxiliary catheter 32 extends from distal of the connector valve and manipulator 14 through the silicone rubber seal 9 to be sealed against the pusher catheter 4 as can be particularly seen in FIG. 4.

The stent graft 6 comprises a tubular body 22 of a biocompatible material and a plurality of self expanding stents 24. A proximally extending exposed stent 25 on the stent graft 6 is received on a distally opening capsule 26 on the nose cone dilator 11. The stent graft 6 has a fenestration 27. The indwelling guide wire 34 extends within the lumen of the stent graft 6 and exits the lumen through the fenestration 27 as can be particularly seen in FIG. 2. The auxiliary catheter 32 and dilator 31 terminate just distal of the stent graft 6.

In the process of deployment the wire guide 9 is inserted in the vessel with an introducer needle using, for example, the well-known percutaneous vascular access Seldinger technique. The delivery device 2 is introduced over the guide wire and manipulated up to the deployment site for the stent graft. The handle 7 at the distal end of the pusher catheter 4 remains outside a patient in use and carries the trigger wire release mechanisms 8 used to release at least the proximal end the stent graft 6 retained on the delivery device by the use of trigger wires (not shown).

The auxiliary guide wire 34 is extended through the fenestration 27 during loading of the stent graft onto the delivery device. When the sheath 10 is withdrawn during deployment the auxiliary guide wire 34 can be manipulated to enter a renal artery, for instance, and remain there while the stent graft is partially or fully released from the delivery device.

The dilator 31 can then be advanced over the auxiliary guide wire 34 until it enters the renal artery and then the auxiliary catheter 32 can be advanced over the dilator. The dilator can then be withdrawn and a further delivery device for a side arm stent into the renal artery for instance can be deployed over the auxiliary guide wire 34 through the auxiliary catheter into the renal artery and deployed. Alternatively before withdrawal of the dilator the auxiliary guide wire can be withdrawn and a stiffer guide wire advanced through the dilator and into the renal artery. The dilator can then be replaced with the further delivery device. The main stent graft can be then fully released. By this pre-catheterisation of the fenestration the process of deployment of side arm stents into branch arteries can be simplified.

In essence therefore the placement of the auxiliary catheter or indwelling catheter between the sheath and the pusher catheter enables the pre-catheterisation of a renal artery before a stent graft is fully released.

FIG. 6 shows an alternative embodiment of the invention. FIG. 6 shows a cross section of a pusher catheter and introducer sheath. In FIG. 6 the pusher catheter 50 has two grooves 52 and 54 and an auxiliary catheter or indwelling catheter 56 and 58 is received in each groove 52 and 54. The sheath 60 covers the pusher catheter 50 and the auxiliary catheters or indwelling catheters 56 and 58. The auxiliary catheters or indwelling catheters 56 and 58 can be used to pre-catheterize two fenestrations for the renal arteries while the pusher catheter is still in place. Where more than two fenestrations are used then the can be more than two grooves and auxiliary catheters in each groove.

Figures 7, 8:
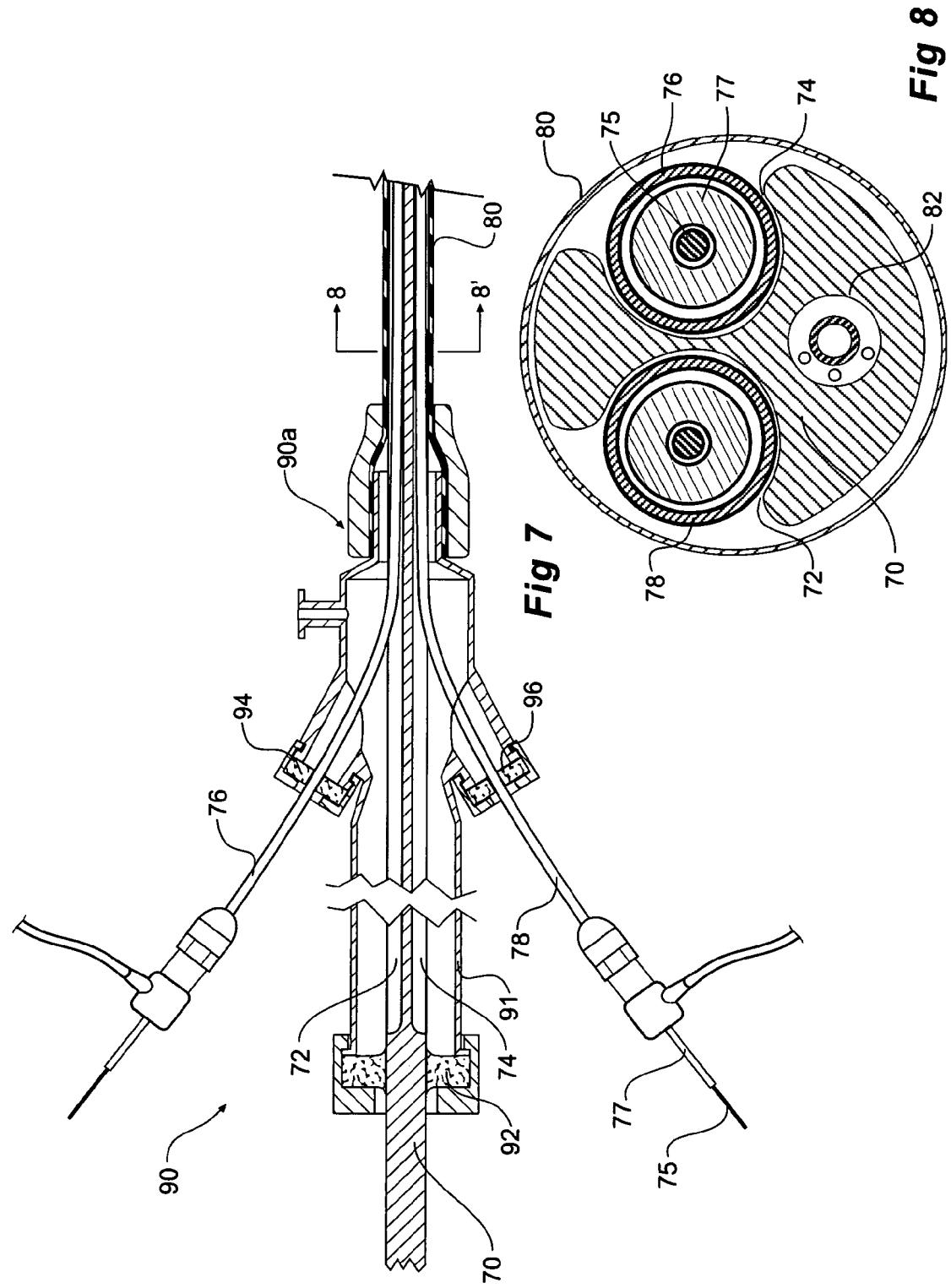
FIG. 7 shows a cross section of a pusher catheter, hemostatic seal and introducer sheath of an alternative embodiment of the invention.
FIG. 8 shows a cross section of a pusher catheter and introducer sheath of the embodiment of the invention shown in FIG. 7.

FIG. 7 shows a longitudinal cross section of a pusher catheter, hemostatic seal and introducer sheath region of an alternative embodiment of deployment device according to the present invention.

In this embodiment the pusher catheter 70 extends from a handle (not shown) into and through a hemostatic seal and valve assembly 90. The pusher catheter 70 has two grooves 72 and 74 and an auxiliary catheter or indwelling catheter 76 and 78 is received in each groove 72 and 74. The grooves 72 and 74 extend proximally from within the hemostatic seal and valve assembly 90. The hemostatic seal and valve assembly 90 includes a seal and valve 92 for the pusher 70 and two auxiliary hemostatic seals 94 and 96 for the auxiliary catheters 76 and 78. The sheath 80 is connected to the proximal end 90a of the hemostatic seal and valve assembly 90. The body 91 of the hemostatic seal and valve assembly 90 is elongate so that as the hemostatic seal and valve assembly 90 is retracted distally to expose a stent graft (not shown) during deployment the indwelling catheters can lay into the elongate grooves 72 and 74 to enable sufficient retraction to expose the stent graft.

FIG. 8 shows a cross section of a pusher catheter and introducer sheath of the embodiment shown in FIG. 7 as shown by the arrows 8-8' in FIG. 7. In FIG. 8 the pusher catheter 70 has two grooves 72 and 74 and an auxiliary catheter or indwelling catheter 76 and 78 is received in each groove 72 and 74. The guide wire catheter lumen 82 is offset from the center of the pusher catheter 70 so that larger grooves 72 and 74 can be provided for the auxiliary catheters 76 and 78. The sheath 80 covers the pusher catheter 70 and the auxiliary catheters or indwelling catheters 76 and 78. Auxiliary guide wires 75 and dilators 77 through the auxiliary catheters 76 and 78 in the same manner as discussed in relation to FIG. 5 and can be used for pre-catheterisation of two fenestrations for the renal arteries, for instance.

FIG. 9 shows a longitudinal cross section of a pusher catheter, hemostatic seal and introducer sheath region of an alternative embodiment of deployment device according to the present invention.

In this embodiment the handle 102 of the introduction device 100 includes a proximal splitter 104 to allow the auxiliary catheters 106 and 108 to separate from the pusher 110 via hemostatic seals 107 and 109. On the introduction device a main sheath 112 extends proximally from a hemostatic seal and manipulator 114. To ensure that the seal portion 114a of the hemostatic seal and manipulator 114 can seal around the pusher 110 with the grooves 110a and 110b and the auxiliary catheters 106 and 108 an auxiliary sheath 116 coaxial with and around the pusher 110 is fastened to the splitter 104 and extends proximally into the hemostatic seal and manipulator 114. By this arrangement the seal 114a can seal around the pusher between the handle 102 and hemostatic seal and manipulator 114.

The main sheath 112 can have a portion 112a of greater diameter to enable the auxiliary sheath 116 to fit inside it as the hemostatic seal and manipulator 114 is retracted. This ensures that the portion of the sheath which contains the stent graft is as low profile as possible.

It can be noted in this embodiment that the auxiliary catheters 106 and 108 with dilators 118 and 120 extend proximally with the dilators terminating just distally of the stent graft 122.

A process for use of the delivery device of one embodiment of the invention is as follows.

In this embodiment the deployment device has the following components:
  guide wire catheter
  main sheath
  nose cone dilator with distally opening top cap
  indwelling guide wire through fenestration and into top cap
  auxiliary catheter on an indwelling guide wire
  auxiliary catheter has a dilator within it extending to a dilator tip stent graft with;
  proximally extending exposed stent
  diameter reducing ties
  distal retention
  renal fenestrations
  radiopaque markers.

Introduction steps are as follows:

(a) Position the deployment device into the aorta correctly taking into account N-S position as well as rotational position with respect to target vessels and fenestrations on the stent graft using markers on stent graft body.

(b) Withdraw the main sheath of the deployment device while continuing to check position until the distal end of the stent graft opens. At this stage the distal end of the stent graft is still retained by distal fixation, the proximal end is retained by the exposed stent retained in top cap of the deployment device and the expansion of the stent graft is restricted by the diameter reducing ties.

(c) Advance the auxiliary catheter and dilator on its indwelling guide wire through the lumen of stent graft to or through fenestration. (At this stage the top cap or capsule is still retaining the exposed stent and the indwelling guide wires).

(d) Position the auxiliary catheter at the opening of the fenestration or at the infundibulum of the fenestration.

(e) Remove the dilator of the auxiliary catheter.

(f) Advance an additional catheter and additional guide wire (4-5 Fr) through the auxiliary catheter and into the target (for instance, renal) vessel. The additional catheter may have a crooked or hockey stick tip to facilitate access.

(g) Remove the guide wire from the additional catheter and re-insert a stiffer wire into the target vessel (renal artery).

(h) Retrieve the indwelling wire guide from the top cap and pull it out completely.

(i) Remove the additional catheter and replace the dilator over the stiffer wire into the target vessel and advance the auxiliary catheter over the stiffer wire into the target vessel. Withdraw the dilator.

(j) Repeat steps (c) to (i) for the other of the target vessels if applicable.

(k) Advance covered stents through the auxiliary catheter into the target vessel but do not release.

(l) Release the diameter reducing ties.

(m) Release the top cap by removing the locking trigger wire and advancing the top cap on the guide wire catheter and release the top exposed stent.

(n) Release the distal attachment of the stent graft.

(o) Withdraw the auxiliary catheter from the target vessels and deploy covered stents between the fenestrations and into the target vessels and balloon expand if necessary including flaring within the main stent graft.

(p) Remove auxiliary catheter and also the guide wire from the target vessel and withdraw them from the system.

(q) Withdraw the entire assembly or leave the main sheath in place for further deployments. Further deployment may include a bifurcated distal component.

Throughout this specification various indications have been given as to the scope of this invention but the invention is not limited to any one of these but may reside in two or more of these combined together. The examples are given for illustration only and not for limitation.

Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

What is claimed is:

1. An endovascular delivery device for delivery of a fenestrated stent graft and pre-catheterization of a branch vessel in combination with a stent graft, the delivery device comprising a pusher catheter, the pusher catheter comprising a distal end and a proximal end and a lumen for a guide wire catheter, the guide wire catheter extending through the lumen of the pusher catheter to and through a nose cone dilator at a proximal end of the guide wire catheter whereby the guide wire catheter is moveable longitudinally and rotationally with respect to the pusher catheter and fixed thereto by the use of a pin vice, a handle at the distal end of the pusher catheter, the stent graft being retained on the delivery device, a flexible sheath over the pusher catheter and extending to the nose cone dilator and thereby retaining the stent graft in a contracted conformation distally of the nose cone dilator, the flexible sheath comprising a proximal end and a distal end, a manipulator and haemostatic seal at the distal end of the flexible sheath, the manipulator and haemostatic seal comprising at least one auxiliary access port, the pusher catheter comprising at least one longitudinal groove on an outside surface thereof, the at least one longitudinal groove extending from the proximal end of the pusher catheter distally to terminate at a distal end within the manipulator and haemostatic seal, wherein the haemostatic seal seals against the pusher catheter distally of the termination of the at least one longitudinal groove, at least one auxiliary catheter extending through the at least one auxiliary access port and proximally between the pusher catheter and the flexible sheath towards the nose cone dilator along the at least one longitudinal groove, the at least one auxiliary catheter comprising a lumen through which a side arm delivery device for a side arm stent can be deployed, a dilator comprising a lumen extending through the lumen of the at least one auxiliary catheter and an auxiliary guide wire extending through the lumen of the dilator, wherein the at least one auxiliary catheter is operable to be advanced over the auxiliary guide wire to a fenestration of the stent graft, thereby to facilitate pre-catheterization of the branch vessel, the stent graft comprising a tubular body of a biocompatible material with a lumen therethrough and a plurality of stents, the stent graft being mounted onto the delivery device for deployment therefrom and being positioned on the guide wire catheter distally of the nose cone dilator and proximally of the pusher catheter and around the guide wire catheter and the auxiliary guide wire passing through the lumen of the stent graft.

2. An endovascular device as in claim 1 wherein the lumen for the guide wire catheter in the pusher catheter is offset from a center of the pusher catheter.

3. An endovascular delivery device as in claim 1 wherein the auxiliary guide wire extendable into the fenestration.

4. An endovascular delivery device as in claim 1 comprising a releasable retention system for a proximal end of the stent graft.

5. An endovascular delivery device as in claim 4 wherein the releasable retention system includes a distally opening capsule at a distal end of the nose cone dilator and an exposed proximally extending stent on the stent graft is received in the capsule.

6. An endovascular delivery device as in claim 1 comprising a plurality of longitudinal grooves in the pusher catheter and a plurality of auxiliary catheters therein.

7. An endovascular delivery device as in claim 1 wherein the at least one auxiliary access port comprises a port haemostatic seal to allow the at least one auxiliary catheter to pass therethrough and be received in the or each longitudinal groove in the pusher catheter.

* * * * *